United States Patent
Salem et al.

(10) Patent No.: US 6,916,891 B2
(45) Date of Patent: Jul. 12, 2005

(54) ATTRITION RESISTANT INORGANIC MICROSPHEROIDAL PARTICLES

(75) Inventors: George F. Salem, Aurora, IL (US); Robert J. Zagata, Seven Hills, OH (US)

(73) Assignee: The Standard Oil Company, Warrenville, IL (US)

( * ) Notice: Subject to any disclaimer, the term of this patent is extended or adjusted under 35 U.S.C. 154(b) by 164 days.

(21) Appl. No.: 10/051,002

(22) Filed: Jan. 22, 2002

(65) Prior Publication Data

US 2002/0160192 A1 Oct. 31, 2002

Related U.S. Application Data

(60) Provisional application No. 60/272,146, filed on Feb. 28, 2001.

(51) Int. Cl.$^7$ .............................. C08F 2/00; B01J 20/02
(52) U.S. Cl. ............................. 526/86; 526/93; 526/99; 526/101; 526/125; 502/306; 502/317; 502/405; 502/407; 502/411; 502/414; 502/421; 502/431; 428/402

(58) Field of Search .............................. 526/86, 93, 96, 526/99, 101, 125; 502/306, 317, 407, 411, 414, 421, 431; 428/402

(56) References Cited

U.S. PATENT DOCUMENTS

| 3,816,342 A | 6/1974 | Plank et al. ............. 252/455 Z |
| 5,591,688 A | 1/1997 | Blum et al. .................. 502/330 |
| 5,998,329 A | 12/1999 | Derolf et al. ................ 502/407 |
| 6,107,238 A | 8/2000 | Contractor et al. .......... 502/247 |

FOREIGN PATENT DOCUMENTS

| JP | 49/040288 | 4/1974 |

*Primary Examiner*—Samuel A. Acquah
(74) *Attorney, Agent, or Firm*—Norval B. Galloway; Wallace L. Oliver

(57) ABSTRACT

Microspheroidal particles, suitable as fluidized bed catalyst supports, are prepared by incorporating a portion of small, preferably recycled, particles into a slurry of inorganic oxide sol and inorganic particles which is spray dried to form microspheroidal particles.

24 Claims, No Drawings

ATTRITION RESISTANT INORGANIC MICROSPHEROIDAL PARTICLES

CROSS-REFERENCE TO RELATED APPLICATIONS

This application claims the benefit of U.S. Provisional Application No. 60/272,146, filed Feb. 28, 2001, which is incorporated by reference herein.

BACKGROUND OF THE INVENTION

The invention relates to microspheroidal inorganic particles having increased attrition resistance, and particularly relates to increased attrition resistance in microspheroidal inorganic support particles used for fluidized bed catalysts.

Inorganic microspheroidal particles, especially silica-based microspheroidal particles, are useful for a variety of purposes, including catalyst supports such as in fluidized bed catalysts, as well as for other uses. In many applications, increased attrition resistance of these inorganic microspheroidal particles is beneficial. For example, increased attrition resistance is important in the use of inorganic microspheroidal particles as catalyst supports in a fluidized bed system in which a typical fluidized bed reactor process imparts high stress upon catalyst particles. Typically, during fluidized bed operation, catalyst particles are suspended and circulate in a gaseous fluid and impact upon each other and the sides of the reactor, causing attrition. Attrition results in the formation of smaller particles which typically are removed by filtration as waste in the gas recycle system. This waste of catalytic material may be reduced through using improved attrition resistant inorganic microspheroidal particles. Reduction in the formation of these small particles is desirable especially if the catalyst incorporates costly components such as precious metals. Additionally, these small particles are difficult to remove and may cause plugging of reactor gas recycle lines.

Recently, a fluidized bed catalyst system has been described that is especially useful for fluidized bed vinyl acetate production. U.S. Pat. No. 5,591,688, incorporated by reference herein, describes a microspheroidal fluidized bed catalyst support system formed by spray drying a slurry mixture of an inorganic oxide sol with inorganic oxide particles. The preferable inorganic oxide used in these catalyst supports is silica. In the typical production of these supports, small particles (fines) of the support material are formed and are removed from the support production process as waste. A use for these waste fines would be beneficial to reduce or eliminate a process waste stream. A use of these fine particles that would improve the attrition resistance of the finished catalyst support particle would be especially beneficial.

Catalyst materials using microspheroidal particles as catalyst supports conveniently may be used in a variety of chemical reactions to manufacture various useful products. Being particulate, such catalyst material is especially suitable for use in a fluidized bed reactor. In the operation of a fluidized bed reactor, catalyst material is brought to a fluidized state by suspending and circulating the catalyst material throughout the reactor with a fluidizing medium, typically a gas. While in this fluidized state, the catalyst material is contacted with reactants, and upon contact, the reactants form a desired product. Fluidized bed reactors are often preferable over other types of reactors, such as fixed bed reactors, because fluidized bed reactors are typically better at facilitating a more constant reaction temperature, especially for exothermic reactions. Additionally, fluidized bed reactors typically enable a more thorough and more uniform contact of reactants with the catalyst material.

Unfortunately, one disadvantage of a fluidized bed reactor is the stress placed upon the catalyst material during reactor operation. While in a fluidized state, the catalyst material is impacted upon itself and the reactor walls, causing it to fracture and break, in a process known as attrition. During operation of a fluidized bed reactor, attrition of catalyst material causes the production of attritted particles, which, because of their smaller size, are susceptible to being removed from the reactor along with a desired product. Removal of these attritted particles represents a loss of catalyst material from the reactor, thereby requiring its replenishment. Such loss is particularly undesirable when the catalyst materials contain catalytically active components which are very costly, e.g. gold, palladium, or other precious metals. Furthermore, because attritted particles are removed from the reactor along with the product, a filter is typically required to separate these particles from the product. In some cases, the filter may become clogged with attritted, particles thereby necessitating shutdown of the reactor so that the filter may be cleaned or replaced.

It would therefore be desirable to reduce the problems associated with the attrition of catalyst material, especially during its use in a fluidized bed reactor. In particular, it would be desirable to discover a way to impart durability to a catalyst material so that attrition is reduced. This desired quality of durability is herein termed "attrition resistance". Catalyst material having attrition resistance is desirable because of its increased useful lifetime and the reduction of catalyst loss.

The invention provides for microspheroidal particles having improved attrition resistance. The microspheroidal particles of this invention are referred to as "attrition resistant microspheroidal particles". The invention also provides for catalyst material having improved attrition resistance. The catalyst material of this invention is referred to as "attrition resistant catalyst material" and has attrition resistance imparted from incorporation of attrition resistant microspheroidal particles as a catalyst support. The present invention also provides a method of operating a reactor wherein attrition of catalyst material is reduced by use of attrition resistant catalyst material. A reactor operated in accordance with this invention generates a lower amount of attrited particles. Attrition resistant catalyst material is particularly useful in a fluidized bed reactor where formation of attrited particles is an undesirable source of catalyst loss. In addition to catalyst conservation, use of attrition resistant catalyst material reduces clogging of filters designed to separate attrited particles from the product of a fluidized bed reactor.

Attrition resistant microspheroidal particles may be obtained by spray drying a slurry comprising an inorganic sol, an inorganic non-sol, and an attrition modifier. The term "inorganic sol" refers to a metal oxide sol. Metal oxide sols are typically prepared by hydrolysis of a metal alkoxide to form the corresponding metal oxide sol. The term "inorganic non-sol" refers to an inorganic particulate material that is not a metal oxide sol.

In one preferable embodiment of the invention, recyclable material is used as the attrition modifier. This recyclable material may be generated during the manufacture of microspheroidal particles. Microspheroidal particles are conventionally made by spray drying a slurry comprising an inorganic sol and an inorganic non-sol. Typically, a portion of microspheroidal particles made in this manner is not suitable for use as a catalyst support and such a portion is referred to as "recyclable material". For example, some portion of the microspheroidal particles may be undesirably small, especially in a fluidized bed reactor where they are undesirably carried away from the reactor. It has now been surprisingly discovered that recycled material may be used as an attrition modifier by spray drying a slurry containing this recycled material, an inorganic sol and an inorganic non-sol to form attrition resistant microspheroidal particles.

In another embodiment of the invention, attrition modifier is obtained from recyclable material made during the manufacture of attrition resistant microspheroidal particles. Like other microsphere manufacturing processes, there may be a portion of the attrition resistant microspheroidal particles made by the invention which is not suitable for use as a support catalyst material, i.e. recyclable material. For example, some portions of the microspheroidal particles may be undesirably small, especially in a fluidized bed reactor where unacceptably small particles are undesirably carried away from the reactor. Surprisingly, recycled material from attrition resistant microspheroidal particles may also be used as an attrition modifier by spray drying a slurry comprising this recyclable material, an inorganic sol and an inorganic non-sol.

In accordance with the invention, an attrition resistant catalyst material comprises attrition resistant microspheroidal particles as a catalyst support. Attrition resistant catalyst material may be suitably made by applying a catalytically active component to attrition resistant microspheroidal particles. Typically, the catalytically active component is applied by any method of impregnation known in the art. Suitably, the catalytically active component of the attrition resistant catalyst material may be chosen from metals, metal compounds, organometallic compounds, or mixtures thereof which are known to be catalytically active. Specifically, the catalytically active component is suitably gold, palladium, any other precious metal, or mixtures thereof.

In another embodiment of the invention, attrition resistant catalyst material is used in a fluidized bed reactor. In this embodiment, the catalyst materials are suitably placed in a fluidized state by introduction of a fluidizing medium, usually gas, into the reactor. Reactants, typically in the gas phase, may then be introduced to the reactor where they typically contact the attrition resistant catalyst material in a thorough and uniform manner. Upon contact with the catalyst material, the reactants form a desired product which is carried away from the reactor. During reactor operation, some attrition of catalyst material occurs to create attrited particles, but this amount is advantageously reduced by using attrition resistant catalyst material. Although attritted particles are typically carried away from the reactor along with the product, thereby requiring the separation of these attrited particles from the product by use of a filter, clogging of this filter is advantageously reduced by use of attrition resistant catalyst material.

SUMMARY OF THE INVENTION

Microspheroidal particles, suitable as fluidized bed catalyst supports, are prepared by incorporating a portion of small, preferably recycled, particles into a slurry of inorganic oxide sol and inorganic particles which is spray dried to form attrition resistant microspheroidal particles.

DESCRIPTION OF THE PREFERRED EMBODIMENT(S)

Attrition resistant spray dried microspheroidal particles of this invention are produced by spray drying a slurry mixture of inorganic oxide sol and inorganic particles to which an attrition modifier material has been added. After spray drying, the particulate material preferably is dried and calcined. Typically, suitable attrition modifier materials are small microspheroidal particles that have been prepared by spray drying a similar slurry mixture of inorganic oxide sol and inorganic particles. In a preferable process, a portion of small spray dried particles, which have been separated after spray drying, is recycled to the slurry mixture that is used to produce spray dried microspheroidal particles. The incorporation of such smaller particles into the slurry produces microspheroidal particles with increased attrition resistance.

In accordance with this invention, microspheroidal particles are formed by spray drying a slurry of at least one inorganic sol, at least one inorganic non-sol and at least one attrition modifier.

Known spray drying processes may be employed to form the microspheroidal particles. Typically, spray drying processes involve the formation of a slurry which is sprayed out of a small orifice or orifices wherein the slurry is atomized to form tiny droplets. The tiny droplets dry and form a particulate material as they are sprayed into a hot medium which may be a hot gas or oil. Preferably, the medium is hot air. Preferably, the slurry is homogenized before spray drying. A particularly suitable spray drying process is described in U.S. Pat. No. 5,591,688, incorporated by reference herein.

A slurry, preferably an aqueous slurry which is spray dried to form microspheroidal particles, preferably contains inorganic sol in an amount at least about 10 wt. % based on the total weight of the slurry, preferably at least about 50 wt. %. The amount of inorganic non-sol particles may range from up to about 90 wt. % based on the total weight the slurry and preferably ranges from up to about 5 to 50 wt. %.

The preferred inorganic sol is a silica sol such as Nalco silica sol 1060, commercially available from Nalco Chemical Company. The preferred inorganic non-sol is a particulate silica, more preferably a fumed silica such as AEROSIL 200 commercially available from DeGussa Chemical Company.

Typically, the slurry of inorganic sol and non-sol is spray dried at an elevated inlet temperature such as from between about 115° to 280° C., preferably about 130° to 240° C., followed by calcining at a temperature typically ranging from between about 550° to 700° C., and preferably from about 630° to 660° C. Calcining is typically preformed for about 1–5 hours.

Attrition resistant microspheroidal particles are made by use of an attrition modifier. This attrition modifier comprises a particulate material formed in the manner described above for making the microspheroidal particles. Preferably, the attrition modifier comprises a portion of the microspheroidal particles that have a small particle size, which has been removed by size classification from a portion of microspheroidal particles.

When the attrition modifier is intended to be used for manufacture of attrition resistant microspheroidal particles, the particle size of the attrition modifier becomes at least partly dependent upon the desired particle size of the microspheroidal particles to be manufactured. If smaller particle size microspheroidal particles are desired, then an attrition modifier with an appropriate small particle size is preferable. A particularly advantageous mean particle size range for microspheroidal particles, especially those used as a catalyst support in a fluidized bed, ranges from about 20 to 120 $\mu$m, and preferably from about 40 to 100 $\mu$m. Given this advantageous particle size range for microspheroidal particles, the attrition modifier particles may have a mean particle size less than 10 μm and typically less than about 25 μm.

The particle size of the attrition modifier may be controlled in any manner known in the art. Spray drying conditions (e.g. orifice size, spray velocity, rotary atomizer wheel speed, and the like) may be varied according to a desired particle size. Particle sizes and amounts of the spray dried inorganic sol and inorganic non-sol used to make the attrition modifier may be varied according to a desired particle size. If an attrition modifier is made which does not have a desired particle size, the attrition modifier may be milled to obtain the desired particle size. A preferable alternative to milling is placing the attrition modifier on an appropriately sized sieve to separate and isolate a fraction of desirable particle sizes. A preferable alternative to using a sieve is feeding the attrition modifier into a classifier to partition particles of a desired size. A suitable classifier is a cyclonic air classifier wherein smaller particles migrate to the top of the reactor and may be collected as an attrition modifier.

To produce an attrition resistant microspheroidal particle, a sufficient amount of attrition modifier is incorporated into the spray dry slurry. Typically, a sufficient amount of attrition modifier is at least 1 wt. % based on the total weight of the slurry, more preferably at least about 2 wt. %, and most preferably from about 3 wt. %. High amounts of attrition modifier present in the slurry may produce a slurry which is undesirably viscous for spray drying and will not act to increase attrition resistance. Typically, the amount of attrition modifier ranges up to about 15 wt. % based on the total weight of the slurry, more preferably from up to about 10 wt. %, and most preferably from about 5 wt. %.

Water is the preferred medium in which to slurry the aforementioned ingredients to form attrition resistant microspheroidal particles. Typically, the total amount of solids in the slurry is about 20 to 80 wt. % of the slurry, and preferably 40 to 60 wt. % of the slurry.

In another embodiment of the invention the amount of attrition modifier is based on the total weight of solids in the slurry. Total weight of solids refers to that portion of the slurry which is not soluble in water. This solids portion may comprise attrition modifier, inorganic sol, and inorganic non-sol. High amounts of attrition modifier present in the solids portion of the slurry may be difficult to homogenize with the other solids in the slurry, thus resulting in inferior spray dried microspheroidal particles. Accordingly, the amount of attrition modifier is preferably up to 35 wt. % based on the total weight of solids in the slurry, more preferably up to about 30 wt. %, and most preferably from up to about 25 wt. %. Sufficient attrition modifier should be present in the solids portion of the slurry so that attrition resistance is imparted to the resulting spray dried microspheroidal particles. Accordingly, the amount of attrition modifier is preferably at least 5 wt. % based on the total weight of solids in the slurry, more preferably at least about 10 wt. %, and most preferably from about 15 wt. %.

In one embodiment of the invention, the particle size of attrition resistant microspheroidal particles is at least partly dependent upon its intended use. The particle size of the attrition resistant microspheroidal particles may be controlled in any manner known in the art. Spray drying conditions (e.g. orifice size, spray velocity, rotary atomizer wheel speed, and the like) may be varied according to a desired particle size. Particle sizes and amounts of the spray dried inorganic sol, inorganic non-sol and attrition modifier used to make attrition resistant microspheroidal particles may be varied according to a desired particle size. If attrition resistant microspheroidal particles are made which do not have a desired particle size, the fraction of microspheroidal particles having an undesirable particle size may be removed. In a related embodiment, it has been discovered that although this removed fraction may be undesirable for whatever reason, the removed fraction may be advantageously used as an attrition modifier for making a next generation of attrition resistant microspheroidal particles. Removal of undesirable sizes of microspheroidal particles may be performed by placing them on an appropriately sized sieve to separate and isolate the fraction of undesirable particle sizes. A preferable alternative to using a sieve is feeding the attrition modifier into a classifier to separate the particles having an undesirable size. A suitable classifier is a cyclonic air classifier wherein smaller particles migrate to the top of the reactor and are collected.

Particle size typically becomes important when catalytic materials made from such attrition resistant microspheroidal particles are intended for use in a fluidized bed reactor. Depending at least in part on the parameters of the fluidized bed reactor, certain particles sizes typically become undesirable. One parameter that typically influences particle size is velocity of the fluidizing medium. At higher velocities, smaller sized particles are carried away from the reactor and are no longer useable as catalyst. Therefore, if the attrition resistant microspheroidal particles are intended as catalyst supports in a fluidized bed reactor, their particle size should be chosen such that catalyst loss due to the presence of smaller particles is reduced.

When used in a fluidized bed vinyl acetate monomer process, it is typically preferred that at least 50% of the attrition resistant microspheroidal catalyst particles are less than about 105 microns, preferably at least 75% are less than 105 microns and more preferably at least 85% are less than 105 microns. In typical attrition resistant microspheroidal catalyst particles suitable for use in fluidized bed reactors, there may be less than 1 to 5% of particles more than 105 microns. Further, typically less than 50% are less than 44 microns and preferably less than 35% are less than 44 microns. Typical attrition resistant microspheroidal particles for use in fluidized bed reactors may contain about 25 to 30% of the particles less than 44 microns. Typical attrition resistant microspheroidal particles for use in fluidized bed reactors have at least 50% of the microspheroidal particles with mean diameters between 44 and 88 microns. Persons skilled in the art will recognize that particles sizes of 44, 88 and 105 microns are arbitrary measures in that they are based on standard sieve sizes. Particle sizes and particle size distributions may be measured by an automated laser device such as a Microtrac 100.

It has also been observed that larger particle sized microspheroidal particles obtained by spray drying are typically less attrition resistant. Although not intending to be bound by any particular theory, it is believed that these larger sized microspheroidal particles have larger internal voids which promote attrition. Accordingly, the particle size of attrition resistant microspheroidal particles should be suitable for use in a fluidized bed without sacrificing attrition resistance. Typically, the appropriate particle size of attrition resistant microspheroidal particles for use in a fluidized bed reactor is from about 10 to 200 μm, preferably from about 20 to 150 μm, and more preferably from about 20 to 120 μm.

In one embodiment of the invention, the particle size of the attrition modifier is at least partly dependent upon the desired particle size of attrition resistant microspheroidal particles resulting from the incorporation of the attrition modifier. In this embodiment, the ratio of the maximum average diameter of the attrition modifier to the mean diameter of the resulting microspheroidal particles is preferably above about 0.01, and may range from about 0.6 or higher, and preferably is about 0.05 to about 0.5 and more preferably ranges from about 0.1 to about 0.4.

In one embodiment of this invention that is particularly advantageous for a fluidized bed reactor, attrition resistant microspheroidal particles are made and microspheroidal particles having mean diameters less than about 25 μm, more preferably less than 20 μm, are removed. Removal of these undesirable smaller microspheroidal particles is preferably done by use of a cyclonic air classifier. In a related embodiment, it has been discovered that although these smaller microspheroidal particles (i.e. less than about 25 μm or about 20 μm) may be undesirable for use in a fluidized bed reactor, they may be advantageously used as an attrition modifier for making a next generation of attrition resistant microspheroidal particles.

The pore volume of attrition resistant microspheroidal particles also typically becomes important if the microspheroidal particles are intended for use in a fluidized bed reactor. Preferably, the microspheroidal particles should be sufficiently porous to permit gaseous reactants in a fluidized bed reactor to diffuse into the microspheroidal particles and contact catalytic sites incorporated within the microsphere (i.e. the pore volume should preferably be sufficiently high so as to permit gaseous diffusion). However, pore volume is typically limited because microspheroidal particles with an exceedingly high pore volume will typically not have sufficient attrition resistance or will typically not have sufficient surface area for catalytic activity. Typically, microspheroidal particles which are sufficient for use as a catalyst support in a fluidized bed have a pore volume of from about 0.2 to 0.7 $cm^3/g$ as measured by mercury porosimetry. Preferably, microspheroidal particles have a pore volume from about 0.2 to 0.7 $cm^3/g$, more preferably from about 0.4–0.55 $cm^3/g$. Appropriate microsphere surface areas (measured by BET) for sufficient catalytic activity are typically from about 50–200 $m^2/g$, preferably from about 60–125 $m^2/g$.

The pore volume of attrition resistant microspheroidal particles is typically affected by the relative amounts and particle sizes of inorganic sol, inorganic non-sol, and attrition modifier used in the slurry which is spray dried during the manufacture of the attrition resistant microspheroidal particles. For example, larger particle size sols pack less efficiently when compared with smaller particle size sols. Thus, larger particle size sols yield an inorganic microsphere product more desirable for use as a catalyst support owing to its relatively greater mesopore volume and smaller micropore volume. Mesopores are voids in a microsphere which are typically greater than 4500 angstroms. Mircopores are voids in a microsphere which are typically less than 4500 angstroms.

One embodiment of the invention a slurry is made from inorganic sol, inorganic non-sol, and water. The slurry is spray dried and the resulting particles are dried and calcined. (Before spray drying, the slurry is preferably homogenized.) The calcined particles are then sent to a separator wherein the particles are divided into at least two groups. One group represents particles with typically desirable properties for microspheroidal particles to be used as a catalyst support in a fluidized bed reactor. Another group represents particles with typically undesirable properties for microspheroidal particles to be used as a catalyst support in a fluidized bed reactor. The desirable group of particles may be impregnated with a catalytic component to form a catalyst material typically suitable for use in a fluidized bed reactor. The undesirable group of particles, typically the small particle fraction, may be used in a second cycle where they are used as an attrition modifier and are mixed with inorganic sol, inorganic non-sol, and water to make a next generation of slurry and begin a new process cycle. Such a cycle may be repeated several times. The separator is preferably a cyclonic air classifier in which smaller and lighter particles migrate to the top of the classifier and may be removed as an undesirable group of particles. The desirable particles may be used as microspheroidal particles and catalyst support for a catalyst material.

Inorganic sols suitable for use in the invention to make attrition modifier and/or attrition resistant microspheroidal particles may be any metal oxide sol. Inorganic sols are typically prepared by hydrolysis of a metal alkoxide to form the corresponding metal oxide sol. An advantageous inorganic sol useful in this invention comprises particles having a mean diameter greater than 20 nm and up to 100 nm or more. According to the present invention, the inorganic sol may comprise aluminum oxides, zirconium oxides, titanium oxides, iron oxides, cerium oxides, $BaTiSiO_3$, $SrTiO_3$, $PbTiO_3$, silica, silica-alumina, and mixtures thereof. Preferably, the inorganic sol is a silica sol comprising silica particles with a mean diameter of from 5–100 nm, more preferably from 40–80 nm, and most preferably from 50–70 nm. A particularly desirable silica sol for use in this invention is Nalco silica sol 1060, commercially available from Nalco Chemical Company.

Inorganic non-sols suitable for use in the invention to make attrition modifier and/or attrition resistant microspheroidal particles may be any inorganic particulate material which is not an inorganic sol. Typically, inorganic non-sols are aggregates with mean diameters of several hundred nanometers. In turn, aggregates comprise individual particles typically having an average diameter of from 7–11 nm and a surface area of from 100–300 $m^2/g$. Preferably, the inorganic particles are sodium free. According to the present invention, useful inorganic non-sols include aluminum oxides, zirconium oxides, titanium oxides, iron oxides, cerium oxides, $BaTiSiO_3$, $SrTiO_3$, $PbTiO_3$, silica, talc, kaolin, mica, calcium carbonate, barium sulphate, calcium phosphate and mixtures thereof. Preferably, fumed silica is used as the inorganic particles of the present invention. An example of a fumed silica is AEROSIL 200, commercially available from DeGussa Chemical Company.

Further embodiments of the invention relate to attrition resistant catalyst material which comprises attrition resistant microspheroidal particles as catalyst support. In accordance with these embodiments, a catalytically active component is applied to attrition resistant microspheroidal particles. The catalytically active component may be applied to attrition resistant microspheroidal particles by any known method which results in the integration of the catalytically active component with the attrition resistant microspheroidal particles, thereby forming a catalyst material. Preferably, the catalytically active component is applied to the attrition resistant microspheroidal particles by any known method, such as by impregnation. A preferred method of impregnation is described in U.S. Pat. No. 6,358,882 which is incorporated by reference for U.S. patent practice. In a typical procedure, an incipient wetness technique is used to impregnate attrition resistant microspheroidal particles with a solution (or solutions) of catalytically active material or precursors thereof, e.g. salts of the catalytically active material. Preferably, the impregnated microspheroidal particles are dried slowly at an elevated temperature, such as 40 to 80° C., typically for more than about eight hours. If catalytically active precursors such as salts of catalytically active metals are used, such metal salts may be reduced after impregnation to form a catalyst material.

Suitably, the catalytically active component of the attrition resistant catalyst material may be chosen from metals, metal compounds, organometallic compounds, or mixtures thereof which are known to be catalytically active. Preferably, the catalyst component comprises gold, palladium, other precious metals, or mixtures thereof. These precious metals are especially preferred when the catalyst material is intended for the production of a monomer intended for use in the manufacture of a vinyl polymer.

Further embodiments of the invention relate to use of attrition resistant catalyst material in a fluidized bed reactor. In accordance with these embodiments, attrition resistant catalyst material is placed in a fluidized state typically by a fluidized gas. Reactants, typically in the gas phase, are introduced into the reactor and typically contact the attrition resistant catalyst material in a thorough and uniform manner. Upon contact with the attrition resistant catalyst the reactants form a desired product. If a polymer product is desired, a polymerization catalyst is chosen as the catalytically active component of the attrition resistant catalyst material.

In a specific embodiment of this invention, a vinyl acetate monomer is formed by contacting attrition resistant catalyst material in a fluidized state with reactants comprising an alpha olefin, a monocarboxylic acid, and oxygen. The alpha olefin may be chosen from any $C_2$ to $C_6$ alpha olefin or mixtures thereof. The monocarboxylic acid may be chosen from $C_2$ to $C_6$ monocarboxylic acid or mixtures thereof. The oxygen may be introduced with other gases, such as being introduced as a component of air. When ethylene is chosen as the alpha olefin and acetic acid is chosen as the monocarboxylic acid, a vinyl acetate monomer is produced in a method known as acetoxylation.

The fluidized bed reactor may be operated in any manner known in the art but described below are preferable operating parameters, especially for acetoxylation. The reaction temperature is preferably maintained at about 100 to 250° C., preferably 130 to 190° C. The reactor pressure is preferably maintained from about 50 to 200 psig (3 to 14 barg), preferably 75 to 150 psig (5 to 10 barg). Attrition resistant materials are maintained in a fluidized state by sufficient gas flow through the reactor. This gas flow is preferably maintained at a level close to the minimum rate required to maintain the fluidized state. Flow rates exceeding the minimum rate may cause channeling of the gas through the reactor which may undesirably decrease reactor efficiency.

This invention is illustrated, but not limited, by the following Examples.

EXAMPLES

The attrition modifier used in the following examples was made by spray drying an aqueous slurry of Nalco silica 1060 (from Nalco Chemical) with AEROSIL 200 silica (from DeGussa Chemical Company), such that about 80 wt. % of silica in the slurry was due to the addition of Nalco silica 1060, and the remainder being due to the addition of AEROSIL 200. The particles formed from spray drying were calcined, resulting in an attrition modifier.

Comparative Example 1

A starting material was obtained by mixing Nalco silica 1060 (from Nalco Chemical) with AEROSIL 200 (from DeGussa Chemical Company), such that about 80 wt. % of silica in the starting material was due to the addition of Nalco silica 1060 and the remainder being due to the addition of AEROSIL 200. A slurry was made by mixing 20 lbs (9.07 kg) of the starting material with no attrition modifier. The slurry was then spray dried and the resulting particles were calcined to yield microspheroidal particles. The surface area of these microspheroidal particles was measured by single point determination of specific surface area using nitrogen adsorption, continuous plow method, in accordance with ASTM D 4567-94. The pore volume of these microspheroidal particles was determined by mercury intrusion porosimetry in accordance with ASTM D 4284-92.

The microspheroidal particles were then screened using a +63 mesh screen and a −90 mesh screen so that the microspheroidal particles had a particle size between 63–90 microns. An attrition test was then performed in accordance with ASTM D 5757-95. After measuring and determining the initial weight of the microspheroidal particles, the ASTM test involved introducing the microspheroidal particles into a vessel with a cyclone where they were subjected to attrition. Attritted particles were created by attrition of the microspheroidal particles. Those attrited particles that had an average diameter of less than about 25 μm migrated to the top of the vessel where they were collected and weighed. The weight of these collected particles was divided by the initial weight the microspheroidal particles to yield a calculated attrition weight percent.

While this attrition weight percent may be effective for measuring the portion of attrited microspheroidal particles having an average diameter less than 25 μm, it can not measure attrition of microspheroidal particles which result in average diameters greater than 25 μm. Thus, the remaining microspheroidal particles, after the separation and collection of attritted microspheroidal particles with average diameters less than 25 μm, may yet contain attrited microspheroidal particles with average diameters greater than 25 μm. To account for attrited particles with average diameters above 25 μm contained in the remaining microspheroidal particles, a qualified measurement was performed by measuring the initial weight of the remaining microspheroidal particles. The remaining microspheroidal particles were then screened by a +63 mesh so that particles less than 63 μm (all the result of attrition) passed through the screen, while particles greater than 63 μm were retained by the screen. Thus, attritted particles were passed through the screen and removed from the material remaining on the screen. A qualified weight percent was determined by weighing the material remaining on screen and dividing this weight by the initial weight measured before screening. Because the retained material on the screen represents material absent from any attritted particles under 63 microns, higher qualified attrition weight percents represent higher attrition resistance.

Example 2

The process in Example 1 was repeated, except that 23.5 lbs (10.66 kg) and 1.0 lbs (0.45 kg) of attrition modifier were used to make the slurry.

Example 3

The process in Example 1 was repeated, except that 23.5 lbs (10.66 kg) and 1.5 lbs (0.68 kg) of attrition modifier were used to make the slurry.

Example 4

The process in Example 1 was repeated, except that 23.5 lbs (10.66 kg) and 2.0 lbs (0.91 kg) of attrition modifier were used to make the slurry.

Example 5

The process in Example 1 was repeated, except that 23.5 lbs (10.66 kg), 2.0 lbs (0.91 kg) of attrition modifier, and 2.6 lbs (1.18 g) of added water were used to make the slurry.

Example 6

The process in Example 1 was repeated, except that 23.5 lbs (10.66 kg) and 2.5 lbs (1.13 kg) attrition modifier were used to make the slurry.

Example 7

The process in Example 1 was repeated, except that 23.5 lbs (10.66 kg) and 3.0 lbs (1.36 g) of attrition modifier were used to make the slurry.

Example 8

The process in Example 1 was repeated, except that 23.5 lbs (10.66 kg), 3.0 lbs 1.36 kg) of attrition modifier, and 4.0 lbs (1.81 kg) of added water were used to make the slurry.

Example 9

The process in Example 1 was repeated, except that 23.5 lbs (10.66 kg) and 3.5 lbs (1.59 kg) of attrition modifier were used to make the slurry.

Results of these Examples are shown in Table 1.

TABLE 1

| | Slurry Recipe | | | | Attrition Resistance Measurements | | Particle Characteristics | |
|---|---|---|---|---|---|---|---|---|
| Ex. | Starting material (kg) | Attrition Modifier (kg) | Added Water (kg) | Attrition Modifier (Wt. % of the slurry) | Attrition Weight Percent | Qualified Weight Percent | Surface Area ($m^2/g$) | Pore Volume ($cm^3/g$) |
| 1 | 9.07 | Nil | Nil | 0 | 4.1 | 37 | 74.1 | 0.44 |
| 2 | 10.66 | 0.45 | Nil | 4.1 | 3.5 | 58 | 73.7 | 0.46 |
| 3 | 10.66 | 0.68 | Nil | 6.0 | 4.5 | 49 | 73.6 | — |
| 4 | 10.66 | 0.91 | Nil | 7.8 | 3.2 | 78 | 71.7 | — |
| 5 | 10.66 | 0.91 | 1.18 | 7.1 | 4.1 | 68 | 66.0 | 0.48 |
| 6 | 10.66 | 1.13 | Nil | 9.6 | 2.2 | 85 | 69.9 | 0.48 |
| 7 | 10.66 | 1.36 | Nil | 11.3 | 2.5 | 62 | 66.8 | 0.49 |
| 8 | 10.66 | 1.36 | 1.81 | 9.8 | 5.0 | 61 | 67.9 | 0.49 |
| 9 | 10.66 | 1.59 | Nil | 13.0 | 2.5 | 88 | 66.7 | 0.51 |

As shown in Table 1, attrition resistance measured by qualified weight percent increased upon addition of an attrition modifier.

What is claimed is:

1. In a method to make attrition resistant microspheroidal particles formed by spray drying an aqueous slurry in the absence of a catalytic metal and comprising a metal oxide sol and an inorganic particulate solid, separating the resulting microspheroidal particles, and drying the microspheroidal particles, the improvement comprising adding a minor portion of added microspheroidal particle lines to the aqueous slurry.

2. The method of claim 1 in which the metal oxide sol and inorganic particulate solid are formed from aluminum oxides, zirconium oxides, titanium oxides, iron oxides, cerium oxides, $BaTiSiO_3$, $SrTiO_3$, $PbTiO_3$, silica, talc, kaolin, mica, calcium carbonate, barium sulphate, calcium phosphate, or mixtures thereof.

3. The method of claim 1 in which the metal oxide sol and inorganic particulate solid are formed from silica.

4. The method of claim 1 in which the microspheroidal particles are formed using up to 35 wt %, based on total solids, of added microspheroidal particle fines in the slurry.

5. The method of claim 1 in which the microspheroidal particles are formed using up to 25 wt %, based on total solids, of added microspheroidal particle fines in the slurry.

6. The method of claim 1 in which the microspheroidal particles are formed using at least 5 wt % and up to 30 wt %, based on total solids, of recycled microspheroidal particle fines in the slurry.

7. The method of claim 1 in which the microspheroidal particles are formed using at least 15 wt % and up to 25 wt %, based on total solids, of recycled microspheroidal particle fines in the slurry.

8. The method of claim 1 in which the ratio of the maximum average diameter of the added microspheroidal particle fines to the mean diameter of the resulting microspheroidal particles is about 0.01 to about 0.6.

9. The method of claim 1 in which the metal oxide sol and inorganic particulate solid are formed from silica, and using at least 5 wt % and up to 25 wt %, based on total solids, of added microspheroidal particle fines in the slurry.

10. The method of claim 9 in which the ratio of the maximum the average diameter of the added microspheroidal particle fines to the mean diameter of the resulting microspheroidal particles is about 0.1 t about 0.4.

11. Attrition resistant microspheroidal particles formed by spray drying an aqueous slurry in the absence of a catalytic metal and comprising a metal oxide sol and an inorganic particulate solid, in which a minor portion of microspheroidal particle fines is added to the aqueous slurry.

12. The microspheroidal particles of claim 11 in which the metal oxide sol and inorganic particulate solid are formed from silica.

13. The microspheroidal particles or claim 12 in which the metal oxide sol is a silica sol.

14. The microspheroidal particles of claim 12 in which the inorganic particulate solid are silica particles.

15. The microspheroidal particles of claim 12 which are formed using at least 5 wt % and up to 25 wt %, based on total solids, of added microspheroidal particle fines in the slurry and in which the ratio of the maximum average diameter of the added microspheroidal particle fines to the mean diameter of the resulting microspheroidal particles is about 0.01 to about 0.6.

16. The microspheroidal particles of claim 11 having a pore volume of 0.2 to 0.7 $cm^3/g$.

17. The microspheroidal particles of claim 11 having a microsphere surface area of 50 to 200 $m^2/g$.

18. The microspheroidal particles of claim 12 having a pore volume of 0.4 to 0.55 $cm^3/g$ and a microsphere surface area of 60 to 125 $m^2/g$.

19. The microspheroidal particles of claim 12 having a particle size of 10 to 200 μm.

20. The microspheroidal particles of claim 18 having a particle size of 20 to 150 μm.

21. A fluidized bed, acetoxylation catalyst component comprising attrition resistant microspheroidal particles of claim 11 on which has been placed catalytic metals.

22. The catalyst component of claim 21 in which the catalytic metals comprise gold, palladium, or mixtures thereof.

23. A method of using the catalyst component of claim 21 in which ethylene, acetic acid oxygen, and the catalyst component are contacted in a fluidized bed under acetoxylation conditions to produce vinyl acetate.

24. The method of claim 1 in which the ratio of the maximum average diameter of the added microspheroidal particle fines to the mean diameter of the resulting microspheroidal particles is about 0.05 to about 0.5.

* * * * *